United States Patent [19]
Stuart et al.

[11] Patent Number: 5,843,719
[45] Date of Patent: *Dec. 1, 1998

[54] CELLUBREVIN HOMOLOG

[75] Inventors: Susan G. Stuart, Montara; Phillip R. Hawkins, Mountain View; Jeffrey J. Seilhamer, Los Altos Hills, all of Calif.

[73] Assignee: Incyte Pharmaceuticals, Inc., Palo Alto, Calif.

[*] Notice: The term of this patent shall not extend beyond the expiration date of Pat. No. 5,650,280.

[21] Appl. No.: 897,429

[22] Filed: Jul. 21, 1997

Related U.S. Application Data

[62] Division of Ser. No. 409,373, Mar. 23, 1995, Pat. No. 5,650,280.

[51] Int. Cl.⁶ .............................. C12P 21/06; C07K 1/00; C07H 21/04
[52] U.S. Cl. ..................... 435/69.1; 530/350; 536/23.5
[58] Field of Search .......................... 435/69.1; 530/350; 536/23.1, 23.5; 935/77, 78

[56] References Cited

U.S. PATENT DOCUMENTS 5,650,280  7/1997  Stuart et al. ................................ 435/6

OTHER PUBLICATIONS

Ralston et al. J Biol Chem (1994) 269:15403–15406.
McMahan et al. Nature (1993) 364:346–349.
Arora. J. Biol. Chem (1994) 269:26165–26171.
Bark et al. PNAS (1994) 91:4621–4624.
Link et al. J Biol Chem (1993) 268:18423–18426.
McMahon et al., "Cellubrevin is a ubiquitous tetanus–toxin substrate homologous to a putative synaptic vesicle fusion protein", *Nature*, 364:346–349 (1993).
Arora, Naveen, "Cytotoxic Effects of a Chimeric Protein Consisting of Tetanus Toxin Light Chain and Anthrax Toxin Lethal Factor in Non–neuronal Cells", *J. Biol. Chem.*, 269:26165–26171 (1994).
Bark et al., "Regulated vesicular fusion in neurons: Snapping together the details", *Proc. Natl. Acad. Sci. USA*, 91:4621–4624 (1994).
Link et al., "Cleavage of Cellubrevin by Tetanus Toxin Does Not Affect Fusion of Early Endosomes", *J. Biol. Chem.*, 268:18423–18426 (1993).
Maniatis et al., *Molecular Cloning, A Labortory Manual*, Cold Spring Harbor Press, Plainview, NY (1989).
Ausubel FM et al., *Current Protocols in Molecular Biology*, John Wiley & Sons, New York, NY (1989).
Hohlfeld P. et al., "Prenatal diagnosis of congential toxoplasmosis with a polymerase chain reaction test on amniotic fluid", *New England Journal of Medicine*, 331:695–699 (1994).
Mulder J. et al., "Rapid and simple PCR assay for quantitation of human immunodeficiency virus type 1 RNA in plasma:Aplication to acute retroviral infection", *J. Clin. Microbiol.* 31:292–300 (1994).
Ralston et al., "Expression of the Synaptic Vesicle Proteins VAMPs/Synaptobrevins 1 and 2 in Non–neural Tissues", *J. Biol. Chem.*, 269:15403–15406 (1994).
Archer et al., "Structures and chromosomal localizations of two human genes encoding synaptobrevins 1 and 2", *J. Biol. Chem.*, vol. 265, No. 28, pp. 17267–17273, (1990).
McMahon et al., "Cellubrevin: a substrate for tetanus toxin found on a constitutive vesicle recycling pathyway is a homologue of synaptobrevin", *Soc. Neurosci. Abst.*, vol. 19, No. 1–3, p.900, (1993).
Sengupta et al., "Identification of novel isoforms of cellubrevin in rat pancreatic acinar cells", *Mol. Biol. Cell.*, vol. 5, p.116A (1994).
Galli et al., "Cellubrevin is not restricted to transferrin receptor–containing vesicles in PC12 cells and colocalizes with synaptobrevin I and II", *Mol. Biol. Cell.*, vol. 5, p.325A (1994).
Galli et al., "Tetanus toxin–mediated cleavage of cellubrevin impairs exocytosis of transferrin receptor–containing vesicles in CHO cells", *J. Cell. Biol.*, vol. 125, No. 5, pp. 1015–1024 (1994).
Jacobsson et al., "Identification of synaptic proteins and their isoform mRNAs in compartments of pancreatic endocrine cells", *Proc. Natl Acad. Sci.*, 91:12487–12491 (1994).
Sudhof et al., "A synaptic vesicle membrane protein is conserved from mammals to Drosophila", *Neuron*, 2:1475–1481 (1989).

*Primary Examiner*—Lisa B. Arthur
*Attorney, Agent, or Firm*—Sheela Mohan-Peterson; Lucy J. Billings; Incyte Pharmaceuticals, Inc.

[57] ABSTRACT

The present invention provides nucleotide and amino acid sequences that identify and encode a novel cellubrevin (CB). The present invention also provides for antisense molecules to the nucleotide sequences which encode CB, expression vectors for the production of purified CB, antibodies capable of binding specifically to CB, hybridization probes or oligonucleotides for detecting the upregulation of CB encoding nucleotide sequences, genetically engineered host cells for the expression of CB, diagnostic tests for activated, inflamed or diseased cells and/or tissues based on CB-encoding nucleic acid molecules and antibodies capable of binding specifically to CB.

3 Claims, 3 Drawing Sheets

```
5' ATG GAG GAA GCC AGT GAA GGT GGA AAT GAT CGT TTG CGG AAC CTG CAA AGT
   M   E   E   A   S   E   G   G   N   D   R   L   R   N   L   Q   S
       9              18              27              36          45      54

GAG GTG GAG GGA GTT AAG AAT ATT ATG ACC CAG AAT GTG GAG CGG ATC CTG GCC
 E   V   E   G   V   K   N   I   M   T   Q   N   V   E   R   I   L   A
 63              72              81              90              99     108

CGG GGG GAA AAC TTG GAA CAT CTC AAC CGC AAG ACA GAG GAT CTG GAA GCC ACA
 R   G   E   N   L   E   H   L   N   R   K   T   E   D   L   E   A   T
117             126             135             144             153    162

TCT GAG CAC TTC AAG ACG ACA TCG CAG AAG GTG GCT CGA AAA TTC TGG TGG AAG
 S   E   H   F   K   T   T   S   Q   K   V   A   R   K   F   W   W   K
171             180             189             198             207    216

AAC GTG AAG ATG ATT GTC CTT ATC TGC GTT TTT ATC ATC ATC ATC CTC TTC
 N   V   K   M   I   V   L   I   C   V   F   I   I   I   I   L   F
225             234             243             252             261    270

ATT TGT GCT CTT TGC CAC TGG TGC CTT CTT CTT AAG TAA 3'
 I   C   A   L   C   H   W   C   L   L   L   K   *
279             288             297            306
```

CELLUBREVIN HOMOLOG

This application is a divisional application of application Ser. No. 08/409,373, filed Mar. 23, 1995, U.S. Pat. No. 5,650,280.

FIELD OF THE INVENTION

The present invention is in the field of molecular biology; more particularly, the present invention describes the nucleic acid and amino acid sequences of a novel cellubrevin homolog derived from cells of rheumatoid synovium.

BACKGROUND OF THE INVENTION

Overview

Rheumatoid arthritis (RA) is a complex disease of uncertain etiology which is distinguished by chronic inflammation of the joints. This disease ultimately leads to massive destruction of articular structures and is particularly important in the destruction of cartilage, the key load-bearing tissue of the joint (cf Isselbacher K. J. et al (1994) Harrison's Principles of Internal Medicine, McGraw-Hill, New York City (NYC) pp. 1648–55).

RA has been most intensively studied in the knee joint. Examination of the rheumatoid knee reveals a far different population of cells than is present in the normal knee. In RA, striking disruption of the regular organization of the normal synovial lining results in the invasion of tissue called pannus into the joint space. Pannus is comprised largely of fibroblast cells; however, the fibroblasts of the pannus exhibit an activated phenotype quite different from normal synovial fibroblasts. RA joints are also characterized by the abnormal occurrence of T and B lymphocytes, monocyte/macrophages, and mast cells. There is evidence that each of these cell types plays an important role in the chronic pathology of RA.

There is strong epidemiological evidence for T-cell involvement in RA. Significant correlations have been demonstrated between several HLA-DR genotypes and susceptibility to RA. These correlations have been taken as evidence of an immunological aspect to RA, and several models have been developed. These models have in common the generation of an immune response against antigens present in the rheumatoid joint. There is some evidence that the initial response may have been to viral antigens. In this scenario, ongoing immune response may be due to low levels of antigen persisting in the joint or a crossreaction to joint structures. Alternatively, the immunologic activity observed in RA may occur in response to the gradual damage and exposure of joint structures.

Evidence also points to the B lymphocyte as an important player in the etiology of RA. A hallmark of RA is the presence of rheumatoid factor (RF), an immune complex between disease-associated polyclonal antibodies and monospecific antibody which recognizes autologous Fc. These polyclonal antibodies may be induced by any number of sources with the subsequent production of antigen as discussed above.

The macrophage is almost certainly an important effector cell in the pathological mechanisms initiated by T and/or B lymphocytes. The macrophage elicits destructive mechanisms by elaborating powerful oxidants and a range of tissue destroying proteases. The macrophage also secretes a variety of cytokines which in turn recruit and activate other inflammatory cells.

Cellubrevin

Cellubrevins are homologues of synaptobrevins, synaptic vesicle-associated membrane proteins (VAMPs). Synaptobrevin was first discovered in rat brain (Baumert et al (1989) Embo J 8:379–84) and initially thought to be limited to neuronal cells. Synaptobrevin is an integral membrane protein of 18 kDA (Ralston E. et al (1994) J Biol Chem 269:15403–6) involved in the movement of vesicles from the plasmalemma of one cell, across the synapse, to the plasma membrane of the receptive neuron. This pathway and the endocytotic process may be blocked by the highly specific action of clostridial neurotoxins which prevents neurotransmitter release by cleaving the synaptobrevin molecule. Synaptobrevins are now known to occur and function in the receptor-mediated endocytotic pathways of many non-neuronal cell types.

Cellubrevins are 16 kDa proteins first found and investigated in rat cells and tissues (McMahon H. T. et al (1993) Nature 364:346–9). In vitro studies of various cellular membranes (Galli et al (1994) J Cell Biol 125:1015–24; Link et al (1993) J Biol Chem 268:18423–6) have shown that VAMPS including the cellubrevins are widely distributed and are important in membrane trafficking. They appear to participate in axon extension via exocytosis during development, in the release of neurotransmitters and modulatory peptides, and in endocytosis. Endocytotic vesicular transport includes such intracellular events as the fusions and fissions of the nuclear membrane, endoplasmic reticulum, Golgi apparatus, and various inclusion bodies (peroxisomes, lysosomes, etc).

Endocytotic processes appear to be universal in eukaryotic cells as diverse as yeast, *Caenorhabditis elegans,* Drosophila, and humans. The homologous proteins which direct the movement of vesicles within and between the cells of these organisms contain evolutionarily conserved domains. Generally, VAMPs have a three domain organization. The domains include a variable proline-rich, N-terminal sequence of 28 amino acids, a highly conserved central hydrophilic core of 69 amino acids, and a hydrophobic sequence of 23 amino acids presumed to be the membrane anchor.

As mentioned for synaptobrevin above, cellubrevins are sensitive to selective proteolysis by metalloendoproteases such as the zinc endoprotease which comprises the light chain of tetanus toxin. Experiments have shown that endosome fusion may continue even after specific cellubrevin cleavage through temperature- and ATP-dependent docking and fusion processes involving N-ethylmaleimide-sensitive fusion proteins (NSF) and small, soluble attachment proteins (SNAP).

A new cellubrevin homolog was discovered among the partial cDNAs which characterize rheumatoid synovium, Incyte Clone No. 80184. Because tissue distribution and VAMPs are more numerous and widely distributed than initially recognized, research on their differential expression and subcellular localization may turn out to be one of the most fruitful areas for the control or amelioration of diseases and disease symptoms.

Cellubrevins are associated with particular cell types, participate in both intracellular and extracellular pathways, and appear to vary in their abundance and specificity. Elucidation of the interactions of this novel homolog (and associated VAMPs) with docking proteins such as syntaxin and SNAPs of the plasmalemma or the core fusion proteins such as NSF and the synaptotagmins (Bark I. C. and Wilson M. C. (1994) Proc Natl Acad Sci 91:4621–4624)provides a means for the regulation of vesicle trafficking in normal as well as acute and chronic disease situations.

SUMMARY OF THE INVENTION

The subject invention provides nucleotide sequence which uniquely encodes a novel human cellubrevin. The cDNA, herein designated cb, was found within Incyte Clone No. 80184 and encodes a polypeptide designated CB.

The invention also comprises using this CB or its variants to intercede in conditions involving physiologic or pathologic compromise which include the steps of testing a sample or an extract with cb nucleic acids, fragments or oligomers thereof. Aspects of the invention include the antisense DNA of cb; cloning or expression vectors containing cb; host cells or organisms transformed with expression vectors containing cb; a method for the production and recovery of purified CB from host cells; and purified protein, CB, which can be used to generate antibodies for diagnosis or therapy of activated or inflamed cells and/or tissues.

DESCRIPTION OF THE FIGURES

FIG. 1 shows the nucleotide (nt) SEQ ID NO:1 and amino acid (aa) sequence of CB SEQ ID NO 2.

FIG. 3 shows amino acid alignment of CB with synaptobrevin (S63830) SEQ ID NO 3 and cellubrevin (X76199) SEQ ID NO 4. Alignments shown were produced using the multisequence alignment program of DNASTAR software (DNASTAR Inc, Madison Wis.).

DETAILED DESCRIPTION OF THE INVENTION

Definitions

Figure 2:
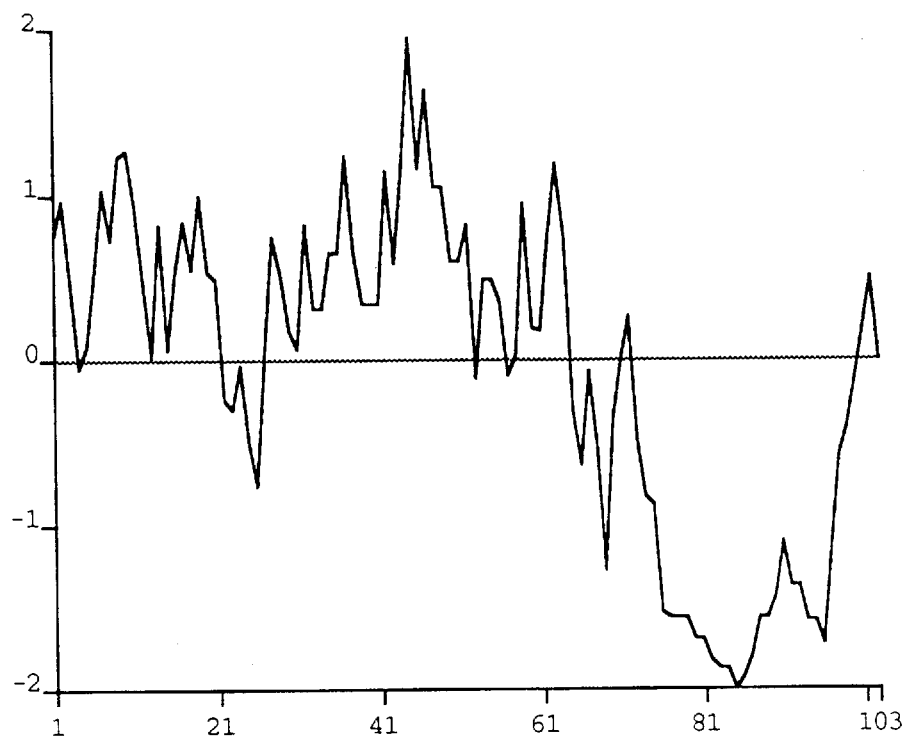
FIG. 2 displays an analysis of CB hydrophobicity based on the predicted aa sequence and composition.

As used herein, CB, refers to cellubrevin polypeptides, naturally occurring CBs and active fragments thereof, which are encoded by mRNAs transcribed from the cDNA (cb) of Seq ID No 1.

"Active" refers to those forms of CB which retain the biologic and/or immunologic activities of any naturally occurring CB.

"Naturally occurring CB" refers to CBs produced by human cells that have not been genetically engineered and specifically contemplates various CBs arising from post-translational modifications of the polypeptide including but not limited to acetylation, carboxylation, glycosylation, phosphorylation, lipidation and acylation.

"Derivative" refers to CBs chemically modified by such techniques as ubiquitination, labeling (e.g., with radionuclides, various enzymes, etc.), pegylation (derivatization with polyethylene glycol), and insertion or substitution by chemical synthesis of amino acids (aa) such as ornithine, which do not normally occur in human proteins.

"Recombinant variant" refers to any polypeptide differing from naturally occurring CBs by aa insertions, deletions, and substitutions, created using recombinant DNA techniques. Guidance in determining which aa residues may be replaced, added or deleted without abolishing activities of interest, such as cellular trafficking, may be found by comparing the sequence of the particular CB with that of homologous peptides and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in a CB molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 amino acids, often at least about 7 aa, typically at least about 9 to 13 aa, and, in various embodiments, at least about 17 or more aa. To be active, any CB polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

The present invention comprises purified CB polypeptide from natural or recombinant sources, cells transformed with recombinant nucleic acid molecules encoding CB. Various methods for the isolation of CB polypeptide may be accomplished by procedures well known in the art. For example, such a polypeptide may be purified by immunoaffinity chromatography by employing the antibodies provided by the present invention. Various other methods of protein purification well known in the art include those described in Deutscher M. (1990) Methods in Enzymology, Vol 182, Academic Press, San Diego; and in Scopes R. (1982) Protein Purification: Principles and Practice, Springer-Verlag, NYC, both incorporated herein by reference.

"Recombinant" may also refer to a polynucleotide which encodes CB and is prepared using recombinant DNA techniques. The DNA which encodes CB may also include allelic or recombinant variants and mutants thereof.

"Oligonucleotides" or "nucleic acid probes" are prepared based on the cDNA sequence which encodes CB provided by the present invention. Oligonucleotides comprise portions of the DNA sequence having at least about 15 nucleotides (nt), usually at least about 20 nts. Nucleic acid probes comprise portions of the sequence having fewer nucleotides than about 6 kb, usually fewer than about 1 kb. After appropriate testing to eliminate false positives, these probes may be used to determine whether mRNAs encoding CB are present in a cell or tissue or to isolate similar nucleic acid sequences from chromosomal DNA as described by Walsh P. S. et al (1992 PCR Methods Appl 1:241–250).

Probes may be derived from naturally occurring or recombinant single- or double-stranded nucleic acids or be chemically synthesized. They may be labeled by nick translation, Klenow fill-in reaction, POR or other methods well known in the art. Probes of the present invention, their preparation and/or labeling are elaborated in Sambrook J. et al (1989) Molecular Cloning: A Laboratory Manual, Cold Spring Harbor Laboratory, N.Y.; or Ausubel F. M. et al (1989) Current Protocols in Molecular Biology, John Wiley & Sons, NYC, both incorporated herein by reference.

"Activated" cells as used in this application are those which are engaged in extracellular or intracellular membrane trafficking, including the export of neurosecretory or enzymatic molecules as part of a normal or disease process.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced or domains of other peptides added to modify the properties of any part of the polypeptide, to change ligand-binding affinities, interchain affinities, or degradation/turnover rate.

DETAILED DESCRIPTION OF THE INVENTION

The present invention provides a nucleotide sequence uniquely identifying a novel human cellubrevin which was expressed in the human rheumatoid synovial tissue. Because CB is specifically expressed in active, and perhaps protective cells, of these tissues, the nucleic acid (cb), polypeptide (CB) and antibodies to CB are useful in investigations of and interventions in physiologic or pathologic processes. Exocytosis governed by CB may direct membrane trafficking within the cell and affect release of chemokines involved in cell migration, proteases which are active in inflammation or other similar activities involving endothelial cells, fibroblasts, lymphocytes, etc. Therefore, a diagnostic test for upregulated expression of CB can accelerate diagnosis and proper treatment of conditions caused by viral or other infections, traumatic tissue damage, hereditary diseases such as arthritis or asthma, invasive leukemias and lymphomas; or other physiologic/pathologic problems associated with abnormal membrane trafficking.

The nucleotide sequence encoding CB (or its complement) have numerous applications in techniques known to those skilled in the art of molecular biology. These techniques include use as hybridization probes, use as oligomers for PCR, use for chromosome and gene mapping, use in the recombinant production of CB, and use in generation of anti-sense DNA or RNA, their chemical analogs and the like. Uses of the nucleotide encoding CB disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of CB-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring CB, and all such variations are to be considered as being specifically disclosed.

Although nucleotide sequences which encode CB and its variants are preferably capable of hybridizing to the nucleotide sequence of the naturally occurring CB gene under stringent conditions, it may be advantageous to produce nucleotide sequences encoding CB or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding CB and its derivatives without altering the encoded aa sequence include the production of RNA transcripts having more desirable properties, such as a greater half-life, than transcripts produced from the naturally occurring sequence.

The nucleotide sequence encoding CB may be joined to a variety of other nucleotide sequences by means of well established recombinant DNA techniques (cf Sambrook J. et al. (1989) Molecular Cloning: A Laboratory Manual, Cold Spring Harbor Laboratory, N.Y.). Useful nucleotide sequences for joining to cb include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for cb-specific nucleic acid hybridization probes capable of hybridizing with naturally occurring nucleotide sequences encoding CB. Such probes may also be used for the detection of cellubrevin receptor encoding sequences and should preferably contain at least 50% of the nucleotides from this cb encoding sequence. The hybridization probes of the subject invention may be derived from the nucleotide sequence of the SEQ ID NO 1 or from genomic sequence including promoter, enhancer elements and introns of the respective naturally occurring cbs. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described in U.S. Pat. Nos. 4,683,195; 4,800,195; and 4,965,188 provides additional uses for oligonucleotides based upon the nucleotide sequences which encode CB. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for cb DNAs include the cloning of nucleic acid sequences encoding CB or CB derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding CB and its derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the cb sequences or any portion thereof.

The nucleotide sequence can be used to construct an assay to detect activation, inflammation, or disease associated with abnormal levels of expression of CB. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for cb can be used to construct hybridization probes for mapping that gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, NYC.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of cb on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

The nucleotide sequence encoding CB may be used to produce purified CB using well known methods of recombinant DNA technology. Among the many publications that teach methods for the expression of genes after they have been isolated is Goeddel (1990) Gene Expression Technology, Methods and Enzymology, Vol 185, Academic Press, San Diego. CB may be expressed in a variety of host cells, either prokaryotic or eukaryotic. Host cells may be from the same species in which cb nucleotide sequences are endogenous or from a different species. Advantages of producing CB by recombinant DNA technology include obtaining adequate amounts of the protein for purification and the availability of simplified purification procedures.

Cells transformed with DNA encoding CB may be cultured under conditions suitable for the expression of cellubrevin and recovery of the protein from the cell culture. CB produced by a recombinant cell may be secreted or may be contained intracellularly, depending on the particular genetic construction used. In general, it is more convenient to prepare recombinant proteins in secreted form. Purification steps vary with the production process and the particular protein produced.

In addition to recombinant production, fragments of CB may be produced by direct peptide synthesis using solid-phase techniques (cf Stewart et al (1969) Solid-Phase Peptide Synthesis, WH Freeman Co, San Francisco; Merrifield J. (1963) J Am Chem Soc 85:2149–2154). In vitro protein synthesis may be performed using manual techniques or by automation. Automated synthesis may be achieved, for example, using Applied Biosystems 431A Peptide Synthesizer (ABI, Foster City, Calif.) in accordance with the instructions provided by the manufacturer. Various fragments of CB may be chemically synthesized separately and combined using chemical methods to produce the full length molecule.

CB for antibody induction does not require biological activity; however, the protein must be immunogenic. Peptides used to induce specific antibodies may have an aa sequence consisting of at least five aa, preferably at least 10 aa. They should mimic a portion of the aa sequence of the protein and may contain the entire aa sequence of a small naturally occurring molecule like CB. Short stretches of CB aa may be fused with those of another protein such as keyhole limpet hemocyanin and antibody produced against the chimeric molecule.

Antibodies specific for CB may be produced by inoculation of an appropriate animal with the polypeptide or an antigenic fragment. An antibody is specific for CB if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R. et al (1989) PNAS 86:3833–3837, or Huse W. D. et al (1989) Science 256:1275–1281) or the in vitro stimulation of lymphocyte populations. Current technology (Winter G. and Milstein C. (1991) Nature 349:293–299) provides for a number of highly specific binding reagents based on the principles of antibody formation. These techniques may be adapted to produce molecules specifically binding CB.

An additional embodiment of the subject invention is the use of CB specific antibodies, receptors or the like as bioactive agents to treat viral or other infections, traumatic tissue damage, hereditary diseases such as arthritis or asthma, invasive leukemias and lymphomas; or other physiologic/pathologic problems associated with abnormal membrane trafficking.

Bioactive compositions comprising agonists, antagonists, or receptors of CB may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that a therapeutic, bioactive composition may be delivered by intravenous infusion into the bloodstream or any other effective means which could be used for treatment.

The examples below are provided to illustrate the subject invention. These examples are provided by way of illustration and are not included for the purpose of limiting the invention.

EXAMPLES

I Isolation of mRNA and Construction of the cDNA Library

The cellubrevin cDNA sequence was identified among the sequences comprising the rheumatoid synovium library (RS). Arthritic synovial joint tissue was obtained when a patient's hip was replaced. The tissue was flash-frozen, ground in a mortar and pestle and lysed immediately in a lysis buffer containing guanidinium isothiocyanate. Lysis was followed by several phenol-chloroform extractions and ethanol precipitation. Poly-A+ mRNA was isolated using a biotinylated oligo d(T) primer and streptavidin coupled to a paramagnetic particle (Promega Poly A Tract Isolation System; Promega Corp, Madison Wis.). The cDNA library was custom prepared by Stratagene (11011 North Torrey Pines Road, La Jolla, Calif. 92037) using a combination of oligo d(T) and random priming. Synthetic adapters were ligated to the blunt-ended cDNA population which was then ligated to the phage lambda-derived Uni-ZAP™ vector (STRATAGENE). This allowed high efficiency unidirectional (sense orientation) lambda library construction and the convenience of a plasmid system with blue/white color selection to detect clones with cDNA insertions.

The quality of the cDNA library was screened using DNA probes, and then, the pBLUESCRIPT® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-BLUE® (Stratagene). The high transformation efficiency of this bacterial strain increases the probability that the cDNA library will contain rare, under-represented clones. Alternative unidirectional vectors might include, but are not limited to, pcDNAI (Invitrogen, San Diego Calif.) and pSHlox-1 (Novagen, Madison Wis.).

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBLUESCRIPT plasmid and the cDNA insert. The phagemid DNA was released from the cells and purified, then used to reinfect fresh bacterial host cells (SOLR, Stratagene), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System DNA Purification System (QIAGEN Inc, Chatsworth, Calif. 91311). This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the RS library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 377 or 373 DNA sequencers).

IV Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S. F. (1993) J Mol Evol 36:290–300; Altschul, S. F. et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologues. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Identification, Full Length Sequencing and Translation of the Gene

Figure 3:
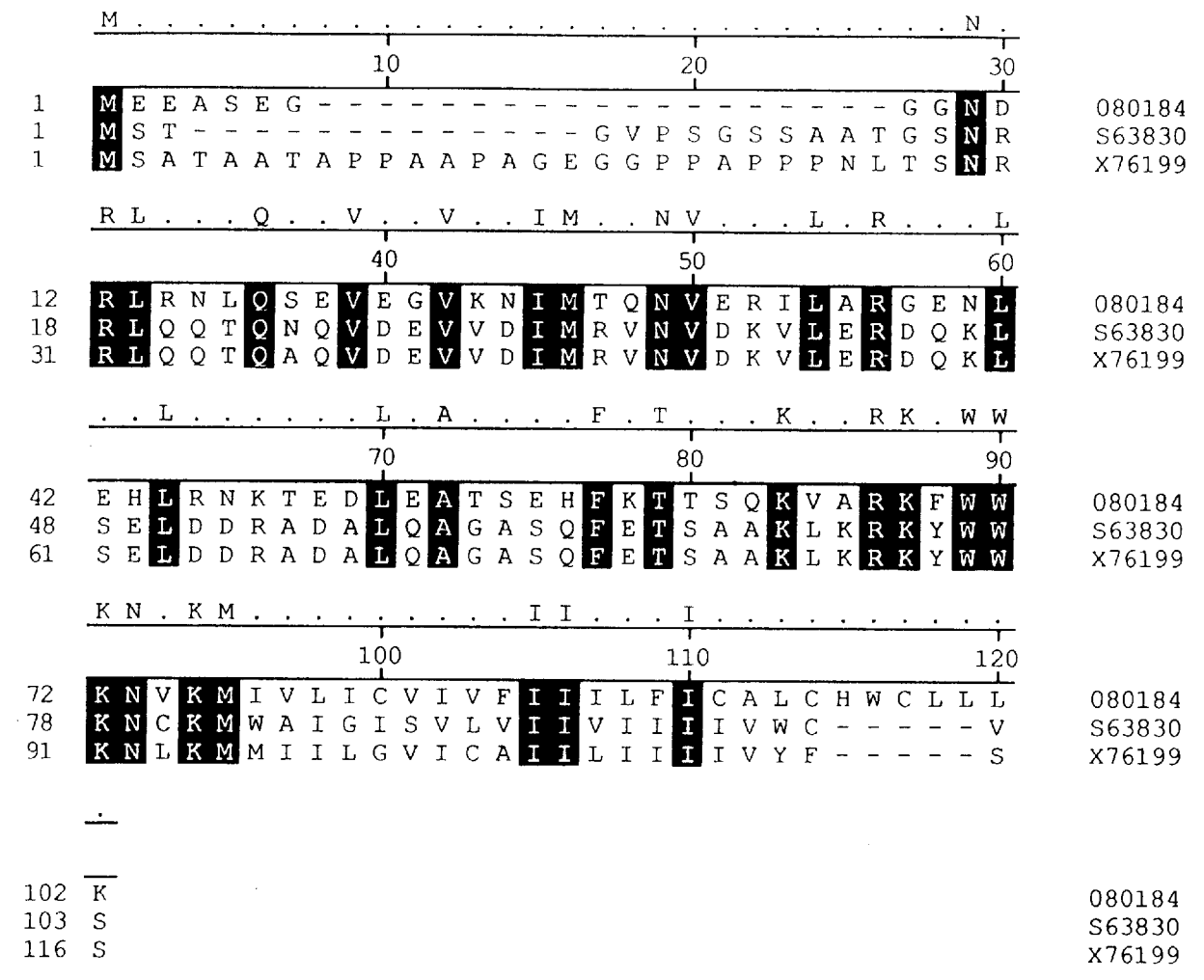

Analysis of the randomly picked and sequenced portions of clones from the RS library identified the cellubrevin sequence in the Incyte 80184 as homologous to cellubrevin from rat (McMahon H. T. et al (1993) Nature 364:346–9). The cDNA insert comprising Incyte 80184 was fully sequenced using the same methods described above. The coding region of the insert (ATG→TGA) was identified and is shown as Sequence ID No. 1. This sequence for human cb was translated using Patent in release 1.30 (an internal U.S. Patent & Trademark Office software package used to comply with sequence rules) and is shown in Sequence ID No. 2. When the translation of the sequence were searched against protein databases such as SwissProt and PIR, no exact matches were found. FIG. 1 shows the nt and aa sequences of CB. FIG. 2 shows the hydrophobicity plot for CB. FIG. 3 shows the amino acid alignment of CB synaptobrevin (S63830 SEQ ID NO3) and cellubrevin (X76199 SEQ ID NO4).

VI Antisense analysis

Knowledge of the correct, complete cDNA sequence of CB will enable its use as a tool for antisense technology in the investigation of gene function. Oligonucleotides, either genomic or cDNA fragments comprising the antisense strand of cb can be used either in vitro or in vivo to inhibit expression of the mRNA. Such technology is now well known in the art, and probes can be designed at various locations along the nucleotide sequences. By treatment of cells or whole test animals with such antisense sequences, the gene of interest can be effectively turned off. Frequently, the function of the gene can be ascertained by observing behavior at the intracellular, cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of CB

Expression of cb may be accomplished by subcloning the cDNAs into appropriate expression vectors and transfecting the vectors into an appropriate expression hosts. In this particular case, the cloning vector previously used for the generation of the tissue library also provide for direct expression of cb sequences in *E. coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The cb cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae,* and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced CB can be recovered from the conditioned medium and analyzed using chromatographic methods known in the art.

VIII Isolation of Recombinant CB

CB may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen) between the purification domain and the cb sequence may be useful to facilitate expression of CB.

IX Production of CB Specific Antibodies

Two approaches are utilized to raise antibodies to CB, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of CB, as deduced from translation of the cDNA, is analyzed to determine regions of high immunogenicity. Oligopeptides comprising appropriate hydrophilic regions, as illustrated in FIG. 2, is synthesized and used in suitable immunization protocols to raise antibodies. Analysis to select appropriate epitopes is described by Ausubel F. M. et al (1989, Current Protocols in Molecular Biology, John Wiley & Sons, NYC). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydxroxysuccinimide ester (MBS; cf. Ausubel F. M. et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled CB to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled CB at 1 mg/ml. Clones producing antibodies will bind a quantity of labeled CB which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual. Cold Spring Harbor Laboratory N.Y.; and in Goding (1986) Monoclonal Antibodies: Principles and Practice, Academic Press, NYC, both incorporated herein by reference.

X Diagnostic Test Using CB Specific Antibodies

Particular CB antibodies are useful for investigation of vesicular trafficking or for diagnosis of infectious or hereditary conditions which are characterized by differences in the amount or distribution of CB, respectively. Since CB has been found in the human umbilical vein endothelial cells (HUVEC), RS, lung and small intestine libraries, it appears to be upregulated in cell types mainly involved in uptake, secretion and systemic protection such as endothelial cell, fibroblasts, lymphocytes, etc.

Diagnostic tests for CB include methods utilizing the antibody and a label to detect CB in human body fluids, membranes, cells, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels. include U.S. Pat. Nos. 3,817,837; 3,850, 752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound CB, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on CB is preferred, but a competitive binding assay may be employed. These assays are described, among other places, in Maddox, D. E. et al (1983, J Exp Med 158:1211).

XI Purification of Native CB Using Specific Antibodies

Native or recombinant CB can be purified by immunoaffinity chromatography using antibodies specific for CB. In general, an immunoaffinity column is constructed by covalently coupling the anti-CB antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns were utilized in the purification of CB by preparing a fraction from cells containing CB in a soluble form. This preparation was derived by solubilization of the whole cell or of a subcellular fraction obtained via differential centrifugation by the addition of detergent or by other methods well known in the art. Alternatively, soluble CB containing a signal sequence may be secreted in useful quantity into the medium in which the cells are grown.

A soluble CB-containing preparation was passed over the immunoaffinity column, and the column was washed under conditions that allow the preferential absorbance of CB (eg, high ionic strength buffers in the presence of detergent). Then, the column was eluted under conditions that disrupt antibody/CB binding (e.g., a buffer of pH 2–3 or a high concentration of a chaotrope such as urea or thiocyanate ion), and CB was collected.

XII Drug Screening

This invention is particularly useful for screening therapeutic compounds by using CB or binding fragments thereof in any of a variety of drug screening techniques. The polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between CB and the agent being tested. Alternatively, one can examine the diminution in complex formation between CB and a receptor caused by the agent being tested.

Thus, the present invention provides methods of screening for drugs or any other agents which can affect vesicular trafficking. These methods comprise contacting such an agent with CB polypeptide or a fragment thereof and assaying (i) for the presence of a complex between the agent and the CB polypeptide or fragment, or (ii) for the presence of a complex between the CB polypeptide or fragment and the cell, by methods well known in the art. In such competitive binding assays, the CB polypeptide or fragment is typically labeled. After suitable incubation, free CB polypeptide or fragment is separated from that present in bound form, and the amount of free or uncomplexed label is a measure of the ability of the particular agent to bind to CB or to interfere with the CB and agent complex.

Another technique for drug screening provides high throughput screening for compounds having suitable binding affinity to the CB polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with CB polypeptide and washed. Bound CB polypeptide is then detected by methods well known in the art. Purified CB can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding CB specifically compete with a test compound for binding to CB polypeptides or fragments thereof. In this manner, the antibodies can be used to detect the presence of any peptide which shares one or more antigenic determinants with CB.

XIII Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf. Hodgson J. (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design efficient inhibitors. Useful examples of rational drug design may include molecules which have improved activity or stability as shown by Braxton S. and Wells J. A. (1992 Biochemistry 31:7796–7801) or which act as inhibitors, agonists, or antagonists of native peptides as shown by Athauda S. B. et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the CB amino acid sequence provided herein will provide guidance to those employing computer modeling techniques in place of or in addition to x-ray crystallography.

XIV Identification of Other Members of the VAMP/SNAP/NSF Complex

The inventive purified CB is a research tool for identification, characterization and purification of receptors, docking and fusion proteins. Radioactive labels may be incorporated into CB by various methods known in the art and used to capture either soluble or membrane-bound receptor molecules. A preferred method involves labeling the primary amino groups in CB with $^{125}$I Bolton-Hunter reagent (Bolton, A. E. and Hunter, W. M. (1973) Biochem J 133: 529). This reagent has been used to label various molecules without concomitant loss of biological activity (Hebert C. A. et al (1991) J Biol Chem 266: 18989; McColl S. et al (1993) J Immunol 150:4550–4555). Receptor-bearing membranes are incubated with the labeled CB molecules, washed to removed unbound molecules, and the receptor-CB complex is quantified. Data obtained using different concentrations of CB are used to calculate values for the number, affinity, and association of receptor-CB complex.

Labeled CB is also useful as a reagent for the purification of a particular molecule with which it interacts. In one embodiment of affinity purification, CB is covalently coupled to a chromatography column. Cells and their membranes are extracted, CB is removed and various CB-free subcomponents are passed over the column. CB-associated molecules bind to the column by virtue of their biological affinity. The CB-complex is recovered from the column, dissociated and the recovered molecule is subjected to N-terminal protein sequencing. This amino acid sequence is then used to identify the captured molecule or to design degenerate oligonucleotide probes for cloning its gene from an appropriate cDNA library.

In another alternate method, antibodies are raised against CB, specifically monoclonal antibodies. The monoclonal antibodies are screened to identify those which inhibit the binding of labeled CB. These monoclonal antibodies are then used in affinity purification or expression cloning of associated molecules.

Other soluble binding molecules are identified in a similar manner. Labeled CB is incubated with extracts or other appropriate materials derived from RS, HUVEG, lung or small intestine cells. After incubation, CB complexes (which are larger than the size of purified CB molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XV Use and Administration of Antibodies, Inhibitors, Receptors or Antagonists of CB Antibodies, inhibitors, receptors or antagonists of CB (or other treatments to limit vesicular trafficking, TCB), can provide different effects when administered therapeutically. TCBs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TCBs include solubility of the molecule, half-life and antigenicity/immunogenicity; these and other characteristics may aid in defining an effective carrier. Native human proteins are preferred as TCBs, but organic or synthetic molecules resulting from drug screens may be equally effective in particular situations.

TCBs may be delivered by known routes of administration including but not limited to topical creams and gels; transmucosal spray and aerosol, transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TCB to be administered, and the pharmacokinetic profile of the particular TCB Additional factors which may be taken into account include disease state (e.g. severity) of the patient, age, weight, gender, diet, time of administration, drug combination, reaction sensitivities, and tolerance/response to therapy. Long acting TCB formulations might be administered every 3 to 4 days, every week, or once every two weeks depending on half-life and clearance rate of the particular TCB.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TCBs and that administration to nerve cells may necessitate delivery in a manner different from that being delivered to vascular endothelial cells.

It is contemplated that conditions or diseases which activate leukocytes may precipitate damage that is treatable with TCBs. These conditions or diseases may be specifically diagnosed by the tests discussed above, and such testing should be performed in suspected cases of viral or other infections, traumatic tissue damage, hereditary diseases such as arthritis or asthma, invasive leukemias and lymphomas; or other physiologic/pathologic problems which deviate from normal cell behavior.

XVI Artificial Vesicles for Delivery of Therapeutic Molecules

The vesicular localization directed by CB and the intracellular and extracellular receptors with which CB interacts was examined using fluorescent antibody. The elucidation of the number, arrangement and specificity of CB in both intracellular and extracellular trafficking is quite valuable. It not only offers the ability to disrupt vesicular processes in disease intervention (arthritis, asthma, cystic fibrosis, etc.), but also allows for the development of artificial vesicles. These vesicles most resemble liposomes and may be sterically stabilized. The particular cellubrevins which they contain act as an address to direct the movement of the vesicle into, through or out of the cell. Both the cellubrevin molecules and the contents of the vesicles are carefully selected. These artificial vesicles will have a particular size and the potential to deliver an antibody, nucleotide or another chemotherapeutic molecule (such as insulin, DNase, etc.). This technology is also potentially useful for the delivery of vectors and recombinant nucleotides to effect a localized, heritable or nonheritable cell therapy. In any of these case, the liposome is addressed to a specific cell type, tissue, organ or tumor.

XVII Chimeric, Therapeutic CB

In another embodiment, the intravesicular end of the CB molecule on an artificial vesicle is chimeric and consists of a therapeutic peptide. Whereas the peptide is protected within the vesicle during delivery; at the time of fusion, it is exposed and effectively becomes part of the intracellular plasmalemma. The exposed peptide either carries out its function while still anchored to the membrane or is cleaved at a predetermined sequence by a constitutive intracellular enzyme and released into the interior of the cell. Delivery of short peptides is specifically contemplated, but should not be considered limiting.

All publications and patents mentioned in the above specification are herein incorporated by reference. The foregoing written specification is considered to be sufficient to enable one skilled in the art to practice the invention. Indeed, various modifications of the above described modes for carrying out the invention which are obvious to those skilled in the field of molecular biology or related fields are intended to be within the scope of the following claims.

We claim:

1. The complement of the polynucleotide sequence shown in SEQ ID NO:1.

2. A method for producing a cellubrevin (CB) having the amino acid sequence of SEQ ID NO:2, said method comprising the steps of:
    a) culturing a host cell transformed with an expression vector comprising the polynucleotide sequence shown in SEQ ID NO:1 under conditions suitable for expression of cb; and
    b) recovering CB from the cell culture.

3. A purified cellubrevin whose amino acid sequence is shown in SEQUENCE ID NO 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 309 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: RHEUMATOID SYNOVIUM
( B ) CLONE: 80184

( x i ) SEQUENCE DESCRIPTION: SEQ ID NO:1:

-continued

```
AGGTGGCTCG  AAAATTCTGG  TGGAAGAACG  TGAAGATGAT  TGTCCTTATC  TGCGTGATTG    60

ATGGAGGAAG  CCAGTGAAGG  TGGAGGAAAT  GATCGTTTGC  GGAACCTGCA  AAGTGAGGTG   120

GAGGGAGTTA  AGAATATTAT  GACCCAGAAT  GTGGAGCGGA  TCCTGGCCCG  GGGGGAAAAC   180

TTGGAACATC  TCCGCAACAA  GACAGAGGAT  CTGGAAGCCA  CATCTGAGCA  CTTCAAGACG   240

ACATCGCAGA  TTTTTATCAT  CATCCTCTTC  ATTTGTGCTC  TTTGCCACTG  GTGCCTTCTT   300

CTTAAGTAA                                                                309
```

(2) INFORMATION FOR SEQ ID NO:2:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: RHEUMATOID SYNOVIUM
        (B) CLONE: 80184

(xi) SEQUENCE DESCRIPTION: SEQ ID NO:2:

```
Met Glu Glu Ala Ser Glu Gly Gly Gly Asn Asp Arg Leu Arg Asn Leu
 1               5                  10                  15

Gln Ser Glu Val Glu Gly Val Lys Asn Ile Met Thr Gln Asn Val Glu
            20                  25                  30

Arg Ile Leu Ala Arg Gly Glu Asn Leu Glu His Leu Arg Asn Lys Thr
        35                  40                  45

Glu Asp Leu Glu Ala Thr Ser Glu His Phe Lys Thr Thr Ser Gln Lys
    50                  55                  60

Val Ala Arg Lys Phe Trp Trp Lys Asn Val Lys Met Ile Val Leu Ile
65                  70                  75                  80

Cys Val Ile Val Phe Ile Ile Ile Leu Phe Ile Cys Ala Leu Cys His
                85                  90                  95

Trp Cys Leu Leu Leu Lys
            100
```

(2) INFORMATION FOR SEQ ID NO:3:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: S63830

(xi) SEQUENCE DESCRIPTION: SEQ ID NO:3:

```
Met Ser Thr Gly Val Pro Ser Gly Ser Ser Ala Ala Thr Gly Ser Asn
 1               5                  10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60
```

```
Glu  Thr  Ser  Ala  Ala  Lys  Leu  Lys  Arg  Lys  Tyr  Trp  Trp  Lys  Asn  Cys
65                  70                      75                           80

Lys  Met  Trp  Ala  Ile  Gly  Ile  Ser  Val  Leu  Val  Ile  Ile  Val  Ile  Ile
                    85                       90                      95

Ile  Ile  Val  Trp  Cys  Val  Ser
               100
```

( 2 ) INFORMATION FOR SEQ ID NO:4:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: X76199

( x i ) SEQUENCE DESCRIPTION: SEQ ID NO:4:

```
Met  Ser  Ala  Thr  Ala  Ala  Thr  Ala  Pro  Pro  Ala  Ala  Pro  Ala  Gly  Glu
1                   5                        10                      15

Gly  Gly  Pro  Pro  Ala  Pro  Pro  Pro  Asn  Leu  Thr  Ser  Asn  Arg  Arg  Leu
               20                       25                      30

Gln  Gln  Thr  Gln  Ala  Gln  Val  Asp  Glu  Val  Val  Asp  Ile  Met  Arg  Val
               35                       40                      45

Asn  Val  Asp  Lys  Val  Leu  Glu  Arg  Asp  Gln  Lys  Leu  Ser  Glu  Leu  Asp
     50                       55                      60

Asp  Arg  Ala  Asp  Ala  Leu  Gln  Ala  Gly  Ala  Ser  Gln  Phe  Glu  Thr  Ser
65                       70                       75                      80

Ala  Ala  Lys  Leu  Lys  Arg  Lys  Tyr  Trp  Trp  Lys  Asn  Leu  Lys  Met  Met
               85                       90                      95

Ile  Ile  Leu  Gly  Val  Ile  Cys  Ala  Ile  Ile  Leu  Ile  Ile  Ile  Ile  Val
               100                      105                     110

Tyr  Phe  Ser  Ser
               115
```